United States Patent [19]

Perl et al.

[11] 4,430,218
[45] Feb. 7, 1984

[54] SEPARATING DEVICE FOR FLUIDS, CONSISTING OF SUPPORT PLATES AND CUT SECTIONS OF A SEMI-PERMEABLE DIAPHRAGM

[75] Inventors: Horst Perl; Dietmar Nussbaumer, both of Göttingen; Hans-Weddo Schmidt, Hardegsen; Günter Pradel; Ulrich Grummert, both of Göttingen, all of Fed. Rep. of Germany

[73] Assignee: Sartorius GmbH, Fed. Rep. of Germany

[21] Appl. No.: 281,931

[22] Filed: Jul. 10, 1981

[30] Foreign Application Priority Data

Jul. 18, 1980 [DE] Fed. Rep. of Germany ....... 3027413

[51] Int. Cl.³ ............................................. B01D 31/00
[52] U.S. Cl. ................................. 210/321.3; 210/346; 210/433.2; 210/450
[58] Field of Search ............... 210/321.1, 321.2, 321.3, 210/321.4, 433.2, 346, 450

[56] References Cited

U.S. PATENT DOCUMENTS

| | | | |
|---|---|---|---|
| 3,831,763 | 8/1974 | Breysse et al. | 210/346 X |
| 4,234,428 | 11/1980 | Schnell | 210/346 X |
| 4,256,692 | 3/1981 | Cover | 210/450 X |
| 4,310,416 | 1/1982 | Tanaka et al. | 210/433.2 X |
| 4,340,475 | 7/1982 | Kraus et al. | 210/433.2 X |

Primary Examiner—Frank A. Spears, Jr.
Attorney, Agent, or Firm—Eric P. Schellin

[57] ABSTRACT

A filtration or diffusion cell, consisting of adjacent facing support plates and cut diaphragm sections of a semi-permeable diaphragm, for the treating fluids. The support plates are sealed by stringlike or bandlike sealing elements for the separate flow conduction of the fluids. Support plates are provided with channel grooves, for holding the sealing elements. The channel grooves are open toward the plate plane and are provided with perforations through which a sealing material inserted in a flowable state and solidified in the grooves. Several support plates are connected by the sealing material to form a plate holder-like unit, and form seals for separate flow conduction. The support plates are square-shaped, and the front side and the back side of the cut diaphragm sections are subjected to crosswise flow of the fluid. The cut diaphragm sections are supported by grooves and groove crests extending in flow direction of the support plates. The grooves are provided with longitudinally spaced passages leading to the opposite side of the support plates. Flow barriers crossing the grooves under an angle of about 45° bring about a uniform overflowing of the diaphragm surfaces and prevent shortcuts.

7 Claims, 13 Drawing Figures

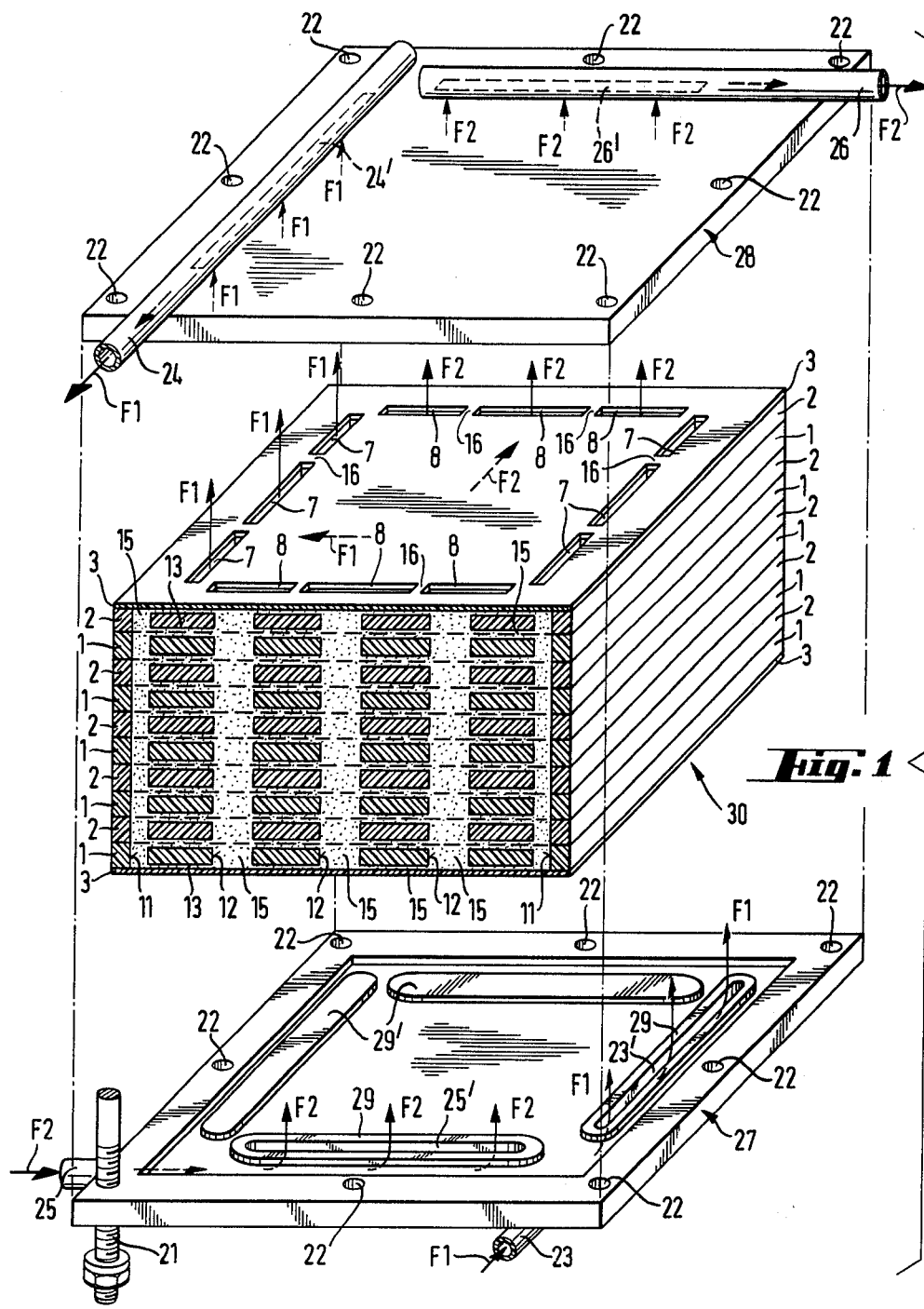

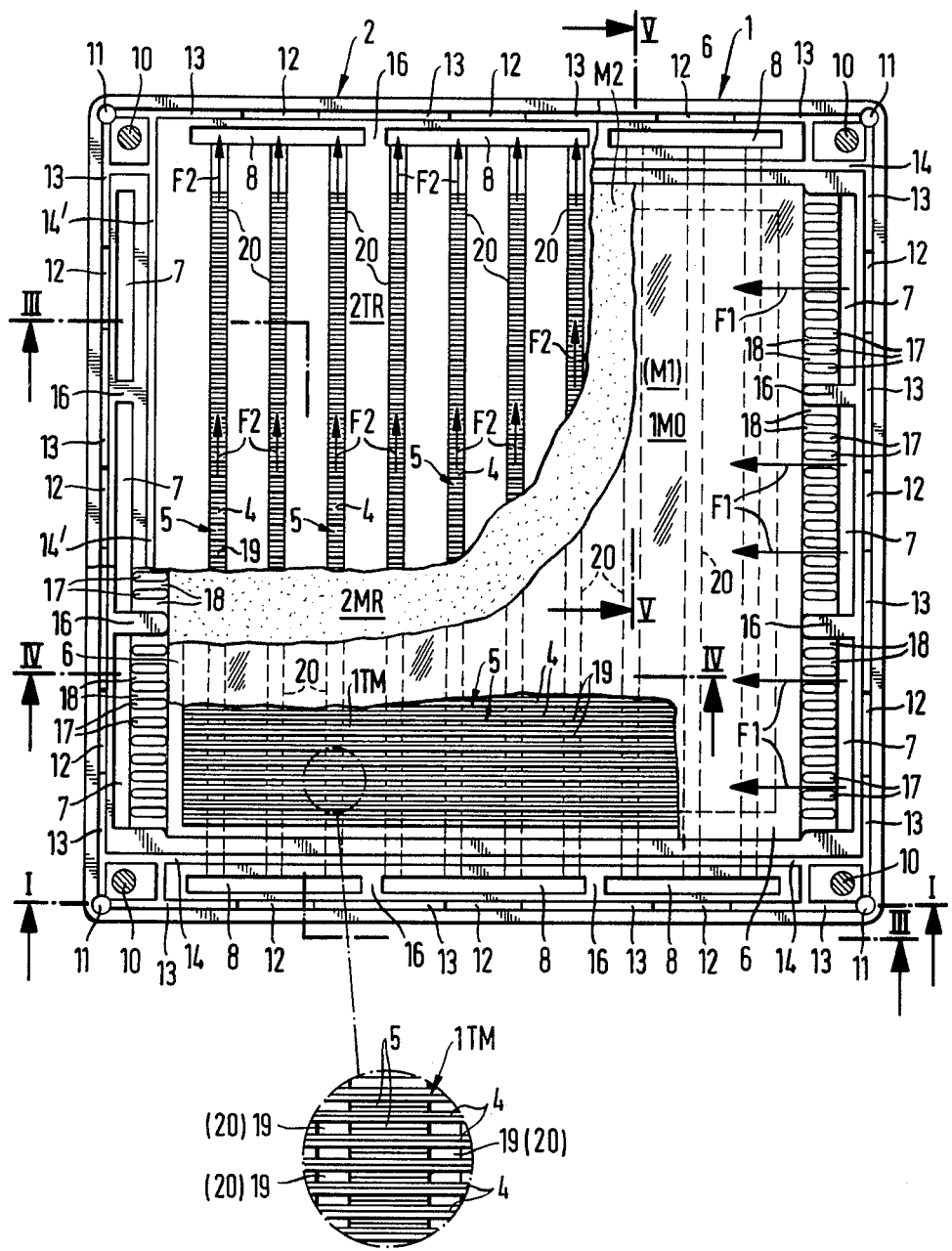

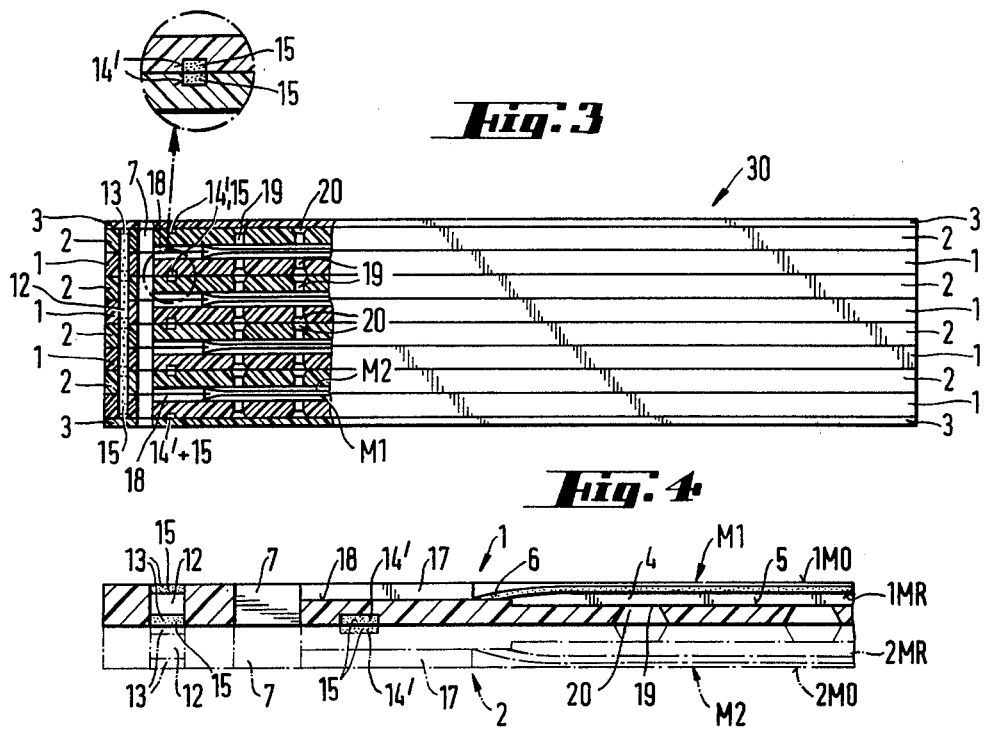

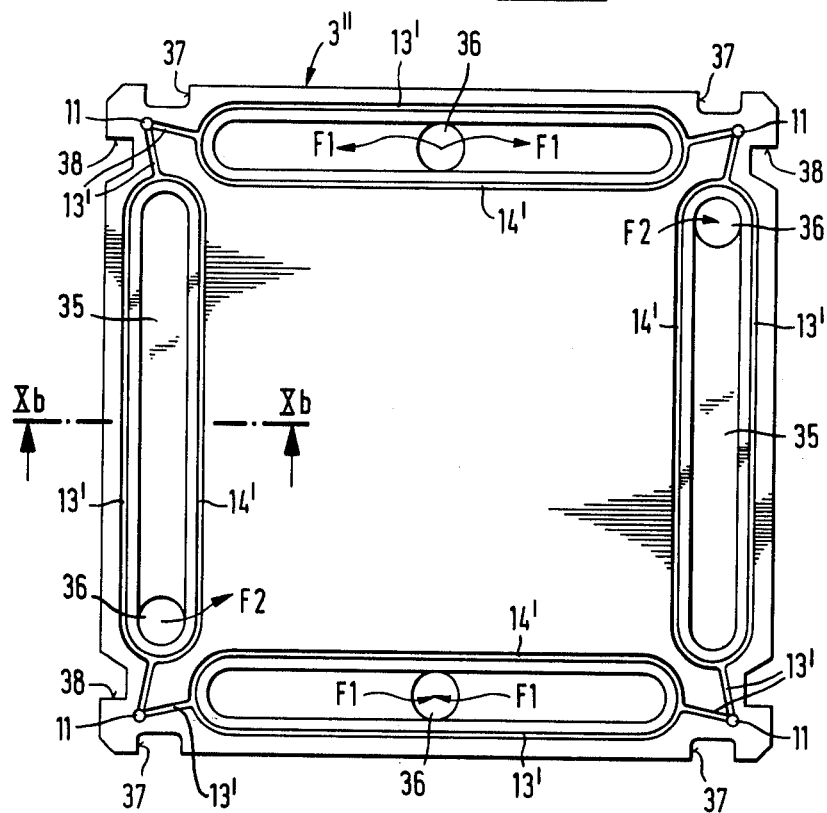

SEPARATING DEVICE FOR FLUIDS, CONSISTING OF SUPPORT PLATES AND CUT SECTIONS OF A SEMI-PERMEABLE DIAPHRAGM

BACKGROUND OF THE INVENTION

The invention relates to a separating device, consisting of support plates and cut sections of a semi-permeable diaphragm, for fluids flowing on both sides of the diaphragm in separate flow paths. The separate flow of the fluids is assured by stringlike or bandlike sealing elements held in the support plates.

In a known separating device disclosed in German (DE-GM 70 22 655), support plates of plastic material are used which are covered by cut diaphragm sections over their whole surface. In the area of the outer border, thin sealing ribs are provided on the support plate, for the separation of the various flow paths and for the total sealing of the flow chambers. The sealing ribs are pressed by the contact pressure into the microporous diaphragm structure. The diaphragm performs sealing function in the area of the sealing rib.

This kind of sealing is unsatisfactory, because of manufacturing tolerances, no plane parallel shaping of the plates and the sealing ribs is possible and the diaphragm must have a certain strength in order to function as a seal.

Depending on the purpose, such as for dialysis, for ultrafiltration, for reverse osmosis, and on the type of the fluids to be treated, be it liquids or gases, special diaphragms must be selected to make an optimum material separation possible. It is therefore known to include, in addition to the support plates, also special sealing plates for better sealing between the individual layers of the support plates as disclosed in U.S. Pat. No. 3,831,763. The sealing frames are flat cut sections of a special sealing material. The special sealing material must—like the diaphragm and the plastic material plates—be capable of being autoclaved repeatedly, therefore no sealing material is suitable for all purposes of the separating device. The support plates of plastic material must have a certain strength so that they are not distorted in the autoclaving and can resist the clamping forces of the total device. The additionally necessary sealing frames raise the cost of the total structure of such a package-like separating device and present additional danger points for the occurrence of leakage.

A more recent concept as disclosed in German (DE-OS 29 30 986) consists in sealing by means of sealing ribs molded into the support plates. Such a sealing becomes problematical in the area of the inlets and outlets which are in most cases shaped as circular bores which penetrate the entire stack of the support plates and are horizontally converted into secondary-distribution channels.

U.S. Pat. No. 3,585,131 discloses a structure in which the support plates slot perforations pass over the entire width of the diaphragm over which the fluid flows, in order to achieve a better distribution of the fluid flows. In this known separating device the diaphragm consists of interwoven hollow fiber diaphragms through which the flow passes crosswise and over which it passes vertically. The fabric-like diaphragm is sealed, for the purpose of separating the three fluid spaces against the support plates, by a plastic material pasting layer. This construction and the sealing is very expensive to manufacture. The fabric-like structure also results in the danger that the sealing material does not satisfactorily penetrate the interspaces of the fabric and envelop the individual hollow fiber diaphragms and seal them off against the support plates.

In deviation from the use of support plates rigid in themselves, it is already known to form separating elements in multilayers from a plastic fabric with a fleece-like support material arranged on both sides, and from the diaphragms arranged on both sides. The sealing of the individual separating units is accomplished by spraying a synthetic resin around the entire outer border of the separating element. The fluid flows are distributed within the separating element through spaced bores arranged at the borders, for the mutual separation of the fluid paths. The adjacent bores are connected alternately on the outside and inside by an arched seal of synthetic resin over the sealed-off outer borders as disclosed in DE-OS 29 20 253 and U.S. Ser. No. 906,922.

This type of seal is also unreliable since it depends essentially on the control and exact limitation of the depth of penetration of the synthetic resin into the individual layers of the separating element.

Reference is also made to U.S. Pat. Nos. 4,113,625, and 3,497,423 which disclose various geometrical forms of the separating elements, sealing elements and support plates.

SUMMARY OF THE INVENTION

Accordingly, it is an object of the invention to produce a separating element composed of a multiplicity of individual elements, with a large effective diaphragm surface which makes possible, in spite of the multiplicity of the individual separating elements, a simple and reliable sealing of the flow paths and flow chambers to be separated and permits a favorable flow of the fluids and a good utilization of the diaphragm surfaces.

This object is achieved, by means of a structure wherein the support plates are provided with channel grooves open toward the plate plane and perforations in these channel grooves which communicate at least sectionwise and hold a sealing material inserted in the flowable state and solidifying therein. The geometrical form of the support plates, the type of the flow of the fluids and the necessary arrangement of the sealing elements depend to a certain extent on each other for the purpose of optimum separating effects, optimum sealing function and optimum manufacture.

This and other objects of the invention will be better understood when taken in connection with the following description and the drawings in which:

BRIEF DESCRIPTION OF THE DRAWINGS

FIG. 1 is a perspective exploded drawing of the total device with a vertical section through the individual separating elements connected to form a block or square-shaped element along section line 1—1 in FIG. 2;

FIG. 2 is a plan view upon two superposed identical support plates with diaphragms, partly as a section of front side and back side;

FIG. 3 is a cross section through a stack of connected separating elements along section line 3—3 in FIG. 3;

FIG. 4 is a partial section through a support plate with diaphragm along line 4—4 in FIG. 2;

FIG. 5 is a longitudinal section through a support plate with diaphragm along line 5—5 in FIG. 2;

FIG. 10a is a plan view of one of the half plates forming the terminal plate in the area of the main connections of the separating device shown in FIG. 7; and FIG. 10b is a cross sectional view of the half plate of FIG. 10a along line Xb—Xb.

DESCRIPTION OF THE PREFERRED EMBODIMENTS

Figure 6:
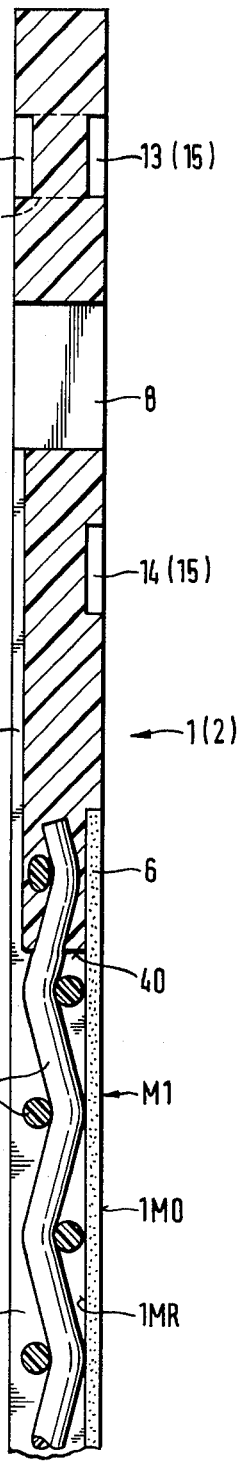
FIG. 6 is a detail section through a support plate with a support element of fabric.

Referring now to the drawings, the separating device is composed of identical support plates which are marked support plate 1 and support plate 2 for better identification. In FIG. 2, each adjacent facing support plate 1, 2 presents essentially a rectangular ground plan and rectangular cross section. Support plates 1, 2 are provided, on all four rectangular sides, with several slot perforations 7,8 which, for reasons of stability, are only interrupted by connecting bridges 16. These connecting bridges 16 may be dispensed within smaller types of support plates.

Slot perforations 7,8 end in each case in the area of the outer borders of diaphragms M1 and M2, so that the fluid flow flowing in slot perforations 7,8 can sweep over diaphragms M1,M2 over their entire width. Support plate 1 is shown from the diaphragm side, and this side is marked 1TM. The diaphragm side of support plates 1,2 is provided with support elements 4 and flow channels 5. In FIG. 5, these elements are formed by grooves and bridges prismlike in cross section, these grooves forming the flow channels 5, and the crests of the bridges forming the support elements 4 for the cut diaphragm sections. Grooves 5 are provided with passages 19 arranged in longitudinal spacing and leading to the opposite side of the support plate 1 or 2, and the passages 19 are widened on the opposite side so as to form connection channels 20 running transversely to the grooves 5. These channels 20 end in the slot perforations 8 for the second fluid. The individual cut diaphragm sections are connected at their border areas 6 peripherally with the support plates. This connection is established in a sealing manner by welding or pasting. In the area between diaphragm borders 6 and slot perforations 7, spacers 17 and gates 18 are provided, which make it possible, on the one hand, for fluid F1 to flow from slot perforations 7 through gates 18 via the diaphragm upper surface 1MO in the direction to the opposite slot perforations 7. The superposed suppport plates are given a mutual sufficient plane parallel support by means of spacers 17. Likewise, the backside of each support plate, shown at 2TR of support plate 2 in essentially plane parallel position, is only interrupted by collecting channels 20. The backsides of support plates 1,2 therefore support each other over a large surface.

Each support plate F1 and F2 is provided, at least at two opposite corners, with perforations 11 for providing a separate passage of the two fluids. In the present embodiment, perforations 11 are provided at all four corners. These opposite perforations 11 are connected by cutoff channels 13 running in both directions. These cutoff channels are arranged on both sides of the support plates. It is, however, sufficient to provide these cutoffs channels 13 on one side of the support plates since the superposition of several support plates assures that between two support plates 1,2 in each case a cutoff channel 13 is provided peripherally. In addition, cutoff channels 11 are provided with further perforations 12, distributed over their length. These perforations 12, one on top of the other, pass through all support plates 1,2 in a shaftlike manner. These perforations 11,12 and the cutoff channels 13 serve for holding the sealing means described below, in order to seal the entire outer area and to establish a stable connection between the superposed support plates 1,2.

In order to seal the fluid space for separate flow of fluid 1 from the flow of fluid 2, there is provided grooves 14, parallel to flow channels 5 outside the border area 6 of diaphragm M1 at the two opposite rectangle sides. The grooves 14 communicate with cutoff channels 13 and/or perforations 11,12. These two grooves 14 are arranged only on the diaphragm support side of support plates 1,2 which is marked 1TM in FIG. 2. On the backsides of support plates 1,2, two corresponding grooves 14' are provided which, however, run parallel to collecting channels 20 and communicate with cutoff channels 13 and/or perforations 11,12. This assures that the permeate emerging at the diaphragm backside can pass through the perforations 19 of support plates 1,2 and can enter slot perforations 8 from collecting channels 20 but not slot perforations 7 through which the first fluid F1 passes. The backside of the diaphragms is marked in FIG. 2, 2MR for diaphragm 2.

In addition there are provided in support plates 1,2, at least in the four corner areas, openings for assembly tightening devices 10 which in the assembly serve first for guiding the support plates 1,2 to be stacked on top of each other.

Support plates 1,2, provided with cut diaphragm sections M1 and M2, are placed upon assembly tightener 10 in pairs and with the diaphragms placed on top of each other, as shown in FIG. 2, and put together to form a stack of 10 or 20 support plates 1,2. With the aid of the assembly tightener 10 and pressing means not shown, the superposed support plates 1,2 are firmly pressed together. All non-recessed surfaces of support plates 1,2 in this structure rest in plane parallel position on the counter-surfaces of the other support plates. In this preassembled state, a sealing means 15 of a flowable synthetic resin, adhesive, or thermoplastic material is injected into the perforations 11. The injection may be made into the left lower perforation 11 as shown in FIG. 2. If the package of support plates 1,2 is positioned so that the diagonal of the two opposite perforations 11 is in vertical position, the injected sealing means 15 rises in both directions in cutoff channels 11 and grooves 14 in the direction of the highest perforation 11 and displaces the enclosed air the hollow spaces formed by perforations 11, cutoff channels 13 and grooves 14,14'. Since the sealing means 15 consists of plastic material, synthetic resin and/or adhesive which is flowable but thermally and/or agehardenable, a stable, tight mutual connection of the individual support plates 1,2 takes place after the hardening of the sealing means, so that after the removal of assembly tightening devices 10 the package-like or square-shaped separating device 30 shown in FIG. 1 is produced which can be clamped-in in a sealing manner as a block between the two end plates 27 and 28.

In order to accelerate the filling of cutoff channels 13 and grooves 14,14' and to achieve an even better sealing of support plates 1,2 to each other over the entire periphery, further perforations 12 are provided in the area of cutoff channels 13. These perforations 12 hold the sealing means 15 in continuous columns as shown in FIG. 1.

In the simplest embodiment, the stack of superposed support plates 1,2 is in each case terminated by the back side of such a support plate. The cut diaphragm section that is positioned closest to the outside in this structure is protected against mechanical damages by the back side of the support plate that is positioned closest to the outside. Packing rings 29 are provided for the sealing connection with the two end plates 27,28.

When the outermost support plates are provided with an additional protection of the cut diaphragm section this is provided by a plane connecting plate 3 on each side of the element 30. The terminal plates 3 have, as shown in FIG. 1, corresponding slot perforations 7,8. Terminal plates 3 may, however, be shaped as flat seals, i.e., they have a certain permanent-elastic effect and perform the sealing function between the package-like end device 30 and the two end plates 27,28, so that no special annular seals 29 are necessary at these end plates.

The main slot perforations 23', 25', 24', and 26' can be provided with annular seals or other flat seals 29, as shown in FIG. 1, unless a special seal is provided on the top and bottom side of the package-like separating device 30. Corresponding seals 28' must then also be provided in the area of the blind connections for the other slot perforations 7,8.

For the carrying-out of an ultrafiltration, only one main connection, either the main connection 25 or the main connection 26, is necessary for the fluid F2. Since the permeate need not flow over the back side of the cut diaphragm sections but must only be withdrawn from the entire surface, it is only necessary to provide slot perforations 8 on the third or fourth rectangle side. In order to assure from a comprehensive application, beginning with support plates 1,2 these support plates are constructed for being overflown on both sides. In the ultrafiltration, it is advantageous to withdraw the permeate in both directions from the back side of the cut diaphragm sections.

Support plates 1,2 are made of plastic material for economic reasons. They may, of course, also be made of refined steel.

Depending on the geometrical plate configuration and construction of the flow paths and arrangement of the necessary sealing elements, it may be sufficient to arrange perforations 11,12 and channel grooves 13, 14, 13',14'—in distribution over the ground plan of the support plates—which communicate with the plate stack so that individual sections are jointly sealed beyond the stack height. In the embodiments shown, the sealing elements are positioned in such a manner that all channel grooves 13, 14, 13', 14' and perforations 11,12 communicate with each other and therefore all plates are jointly sealed by a single injection of plastic material.

For the establishment of a completely satisfactory sealing function, however, it is only necessary to use a plastic material, e.g. silicone, which exerts a sealing function. The joining of the multiplicity of plates to form a plateholder can be effected by other mechanical tightening means.

The separating device can be employed for all industrial separating methods, that it to say as dialyzer, as filter, as oxygenator, for the separation of milk constituents, for water purification, etc., as well as an artificial kidney or lung in the medical field.

By the arrangement of several such square-shaped separating elements 30, the entire diaphragm surface can be modified, by the closing or a row of slot perforations at the outer support plates 1,2 or by a special construction of the terminal plates 3 the individual package-like separating devices 30 can be connected in series of parallel depending on flow technology.

As shown in FIG. 1, the two end plates 27,28 have a somewhat larger surface area, preferably of refined steel and are provided in the border area with several pin holes 22 which hold tightening elements 21. The bottom end plate 27 is provided with a tubular main connection 23 for the introduction of the first fluid F1, which is associated with the slot perforations 7—arranged on the right side—of support plates 1,2. Main connection 23 ends as main connection slot 23' on the top side of bottom end plate 27. In the opposite border area of the top end plate 28, a corresponding main connection 24 with a correspondingly arranged main connection slot 24' is provided which serves as outlet for the first fluid F1 in the embodiment shown. The first fluid F1 entering the main connection 23 fills slot perforations 7, flows in the individual planes over the cut diaphragm sections, enters the opposite slot perforations 8, and is discharged via the top main connection 24. Flow in reverse direction is of course also possible. When the second fluid F2 is to flow over the reverse side of the diaphragm, two further main connections 25 and 26 in the two end plates 27,28 are provided for the fluid F2. The fluid F2 passes in the bottom end plate 27 through main connection 25 into the main slot connection 25' and then to the slot perforations 8. The back sides of the cut diaphragm sections are analagously overflown, and the fluid F2 enters the opposite slot perforations 8 and therefrom the main connection slot 26' and the main connection 26. Here, too, the reverse flow direction is possible.

The main slot perforations 23', 25', 24' and 26' can be provided with annular seals or other flat seals 29, as shown in FIG. 1, unless a special seal is provided on the top and bottom side of the package-like separating device 30. Corresponding seals 28' must then also be provided in the area of the blind connections for the other slot perforations 7,8.

For the carrying-out of an ultrafiltration, only one main connection, either the main connection 25 or the main connection 26 is necessary for the fluid F2. Since the permeate need not flow over the back side of the cut diaphragm sections but must only be withdrawn from the entire surface, it is only necessary to provide slot perforations 8 on the third or fourth rectangle side. In order to assure from a comprehensive application beginning with support plates 1,2, these support plates are constructed for being overflown on both sides. In the ultrafiltration, it is advantageous to withdraw the permeate in both directions from the back side of the cut diaphragm sections.

Figure 8:
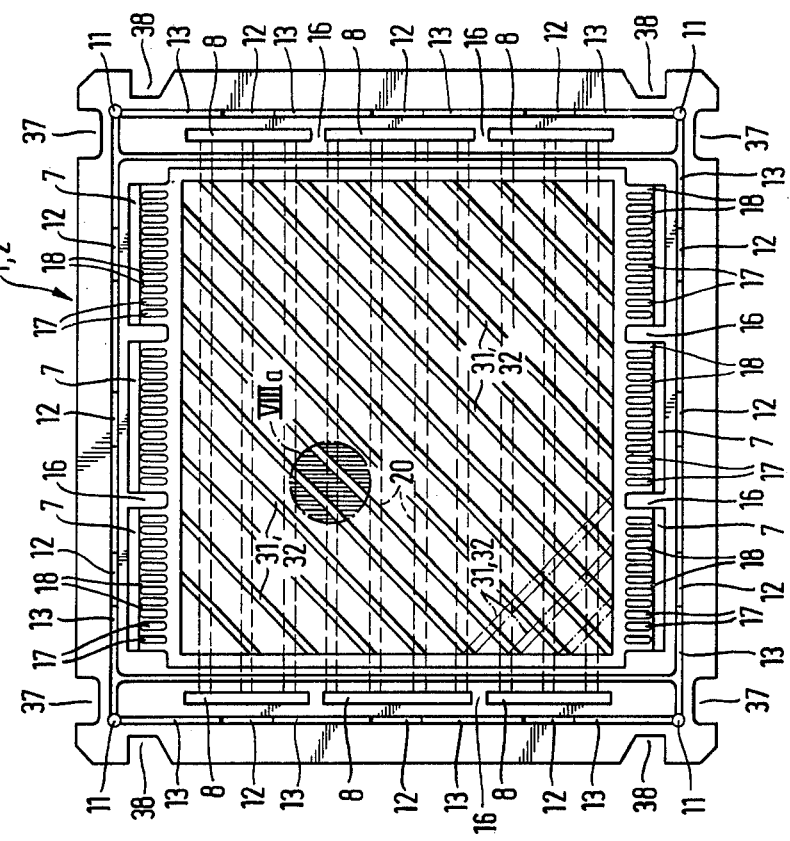
FIG. 8 is a plan view upon a support plate modified to provide optimum flow conditions, upon the diaphragm side.

Support plates 1,2 shown in FIGS. 2, 5 and 8 are particularly suitable for filtration. For the carrying out of separating processes according to the principle of diffusion, more support plates, as indicated in FIG. 6, are suitable. In a material exchange according to the principle of diffusion, it is advantageous to have also the second active fluid F2 come in contact with a surface of the diaphragm as large as possible on the back side thereof. For this purpose, a fabric 39 which supports diaphragm M1 and is fastened in a framelike window 40 of support plate 1 can be used. This may be provided by a construction wherein by thermoplastic defomation of a projection in window 40, the fabric 39 is integrated in the frame of support plate 1 and this area is fastened to the diaphragm outer border 6. In other systems the structure of the support plate corresponds to the detail points represented in FIGS. 2 to 5, as to the form of the flow path and the form of the sealing.

The embodiment according to FIGS. 7 to 10 shows a special separating device as efficient as possible from the viewpoint of easy handling, optimum separating effect and inexpensive manufacture. The structural parts 1 to 10 described above agree functionally with those shown in FIGS. 1 to 6, so that reference can be made to the above statements and described elements concerned.

Figure 7:
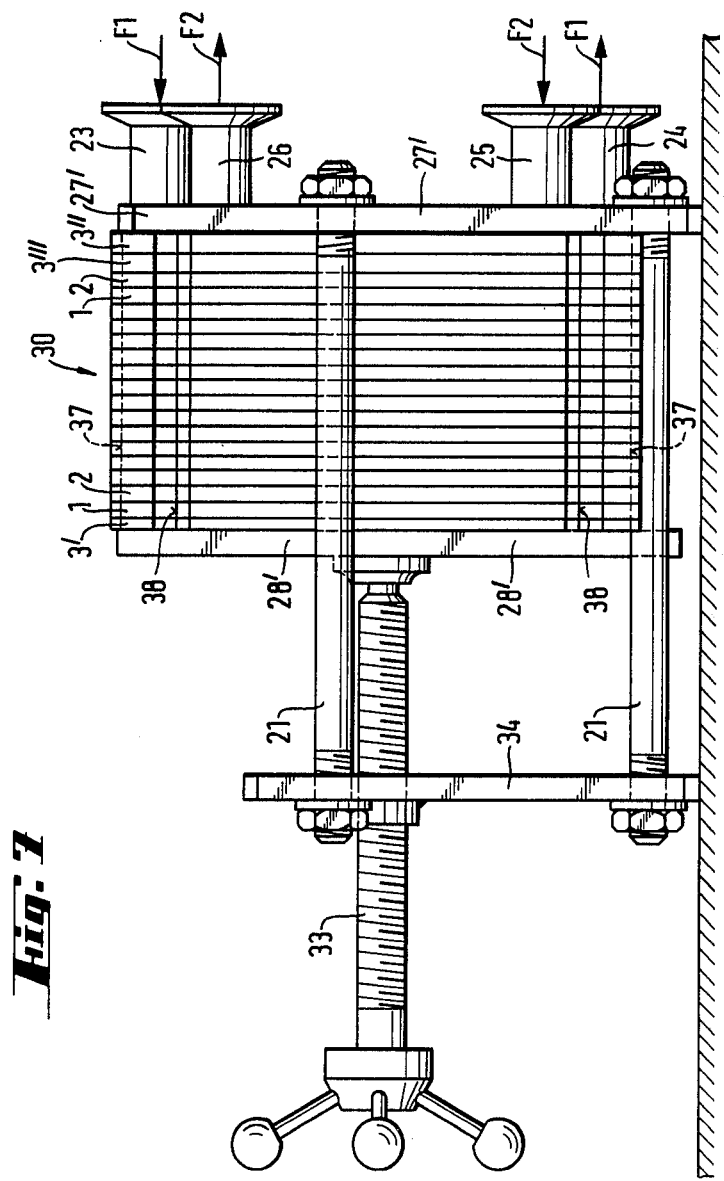
FIG. 7 is in side view a modified total device.

In FIG. 7 the separating device is constructed as upright structure with vertically arranged support plates. The device in FIG. 7 consists of the vertical end plate 27' which contains all four main connections 23 to 26 for the two fluids F1 and F2 and end as bores in end plate 27'. The other end plate 28' extends without connections on the two lower tightening elements 21 displaced in horizontal direction and supported by a central worm-gear spindle 33 which in turn is supported by a vertical abutment plate 34. Abutment plate 34 is connected via four horizontal tightening elements with end plate 27'. The two lower tightening elements 24 serve also as guide and support for the separating device constructed as square-shaped element or as plate holder 30, thus separating device is clamped in between the two end plates 27' and 28'.

Terminal plate 3' which points to connectionless end plate 28' covers the side provided with collecting channels 20 of the last support plate 1 shown in FIG. 2 or FIG. 8 and is integrated therewith through sealing means 15. Terminal plate 3" and 3'" pointing to the connection side is a two-part structure, shown in FIGS. 9 and 10, and described in greater detail as follows: The two-part terminal plate 3" and 3'" is likewise an integrated constituent of the separating device proper, so that support plates 1,2 as well as the two connecting plates 3' and 3",3'" form the plate holder proper 30 which is inserted in a simple manner between the two end plates 27' and 28' as shown in FIG. 7. Guide groove 37 in the plate holder 30 take care of guidance and support on the two bottom tightening elements 21, and molded-in grip grooves 38 facilitate the handling of the plate holder 30 in the insertion between the two end plates 27',28'. Two opposite sides of the plate holder 30 are, in each case, provided with guide grooves 37 and the grip grooves 38, respectively, so that plate holder 30, when turned only by 180° is seated correctly and a faulty insertion is impossible.

This structure presents the advantage that no connections and screws whatsoever need to be detached when a plate holder 30 must be replaced with a new one. This can be accomplished by the detachment of central stem 33.

The construction of the support plate according to FIG. 6, presenting the best possible flow conditions, corresponds in its functional structure to that of the support plate shown in FIGS. 2 to 5 with respect to structural elements 4 to 20.

Figure 8A:
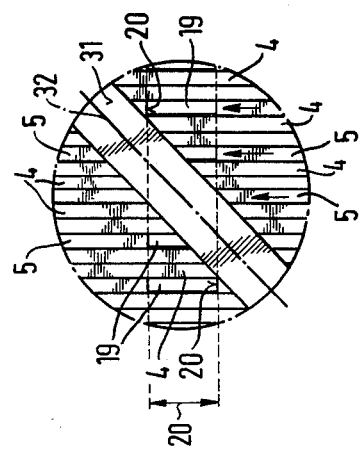
FIG. 8a is an enlarged view of area VIIIa on FIG. 8.

In relatively large-surface support plates 1,2 of plastic material the danger exists that, because of manufacturing tolerances, preferred flow areas form over the total surface of the overflown diaphragm, whereby the effectiveness of the total diaphragm surface suffers. As known from experience, each groove 5 is provided, with reference to the detail point according to FIG. 8a, with several flow barriers 31 arranged in distribution over the groove length. Flow barriers 31 end in the plane of groove crest 4 or below it. In this structure each groove 5 is connected with at least one passage 19 to a crossing collecting cannnel 20 of the opposite side of support plate 1,2.

The multiplicity of the flow barriers 31 are arranged on barrier lines 32 which extend parallel to each other diagonally with respect to grooves 5. In an approximately square diaphragm surface the longest barrier line 32 extends at an angle of about 45° on the diagonal while the other barrier lines 32 are arranged at a distance and parallel thereto. Depending on the ratio of the side lengths of a rectangular diaphragm surface, barrier lines 32 cross grooves 5 at an angle of about 30° to 60°. The barrier lines 32 of two support plates facing each other with their groove side are arranged so as to cross each other. Under the liquid pressure of the over-flowing fluid F1 a certain down-warping of the cut diaphragm sections into the supporting grooves 5 occurs. This is prevented in the area of flow barriers 31, so that at these spots a certain stagnation originates and shortcuts are impossible. On the basis of crossing barrier lines 32 of two plate sides facing each other, the diagonal flow is eliminated again, so that a uniform overflowing of the entire diaphragm surface over the whole oncoming flow side along the slot perforations 7 is assured.

The outer contour of support plates 1,2 deviates from that of FIG. 2 by the provision of guide grooves 37 at opposite outer borders, and by provision of guide grooves 37 likewise at opposite outer borders.

Figure 9B:
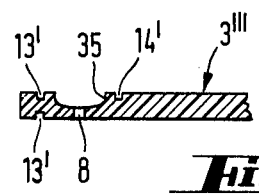
FIG. 9b is a cross sectional view of the half plate of FIG. 9a along line IXb—IXb.
Figure 9A:
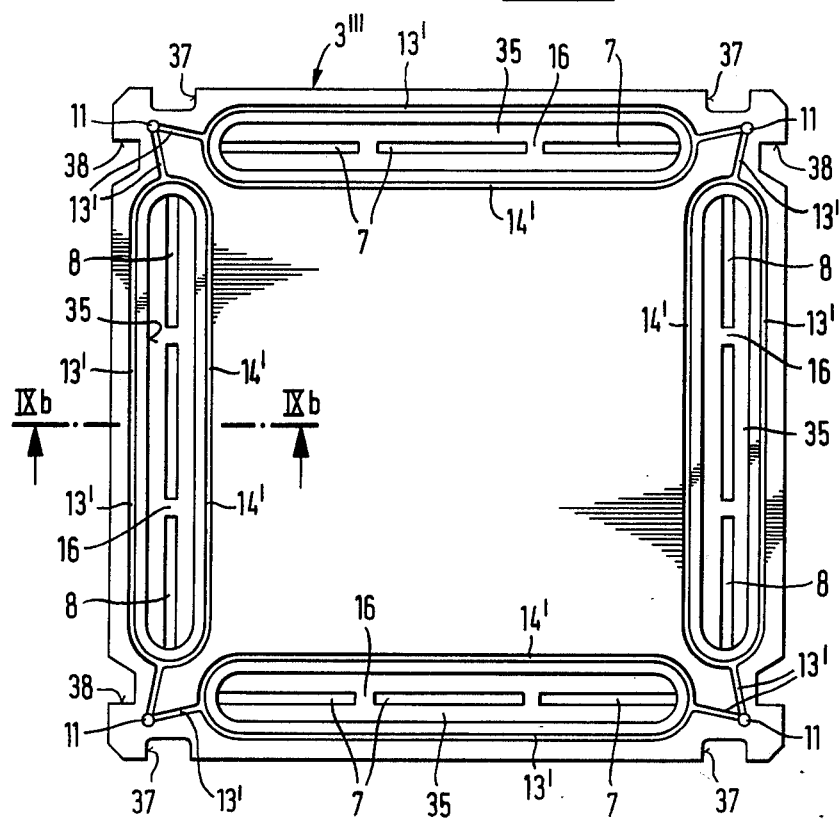
FIG. 9a is a plan view of one of the half plates forming the terminal plate in the area of the main connections of the separating device shown in FIG. 7.

The two-part terminal plate 3"',3" is likewise formed of plastic material and corresponds in its outer contour and slot perforations 7,8 to support plate 1,2 as shown in FIG. 8. The back side, not shown, of the terminal half plate 3'" shown in FIG. 9 is smooth and forms a cover plate 3'" for the uppermost support plate. The back side is provided with the collecting channels 20, as it is indicated in FIG. 2 by 2TR. Grooves 14 and cutoff channels 13 are arranged in the same manner.

As shown in FIG. 9, slot perforations 7,8 are enveloped by distribution and collection pipes 35 which in cross section are approximately trough-shaped and in connection with the coveringly superposed trough shape of the distribution and collection pipes 35 shown in FIG. 10 form a full pipe. Distribution and collection pipes 35 of both terminal plate halves 3'",3" are enclosed by cutoff channels 13' and grooves 14' and connected with the perforations 11 through which the liquid sealing means 15 is injected into all cutoff channels and grooves of all plates of plate holder 30. Terminal plate half 3" corresponds in its structure on the side facing the terminal plate half 3'" to this half and is on the side facing end plate 27' essentially smooth. The bores 36 arranged in distribution and collection pipes 35 are in alignment with the bores of the main connections 23 to 26. Bores 36 are provided, on the side facing end plate 27', with O-ring seals which abut in a sealing manner against end plate 27' when the plate holder 30 is pressed by the central stem 33 against end plate 27'.

We claim:

1. A separating device comprising support plates and cut diaphragm sections of a semi-permeable material, for a first and second fluid flowing on opposite sides of said diaphragm sections in separate flow paths, wherein said support plates are sealed from the outside of said device and additionally sealed to assure the separate flow of the first and second fluid by a sealing means, the support plates are provided with cutoff channel grooves, said cutoff channel grooves of adjacent facing support plates form conduits into which sealling material in a flowable state is injected, the sealing material is injected into said conduits through perforations in said support plates, said perforations communicate with said conduits and other perforations in other adjacent facing support plates, and the sealing material is allowed to solidify in said perforations and said conduits thus forming said sealing means.

2. A separating device as defined by claim 1 wherein said support plates are provided first fluid distribution shafts and second fluid distribution shafts through which the first fluid and the second fluid enter said support plates and said fluids flow on opposite sides of said diaphragm in separate flow paths.

3. A separating device as defined by claim 2 wherein said cutoff grooves are disposed on both sides of the outer border of said support plates.

4. A separating device as defined by claim 3 wherein said cutoff grooves surround the slots for said first fluid and second fluid distribution shafts in said support plates to thereby form said sealing means around said shafts and assure the separate flow of the two fluids.

5. A separating device as defined by claim 4 wherein said cutoff grooves are provided with slot-like perforations into which the flowable sealing material is injected, said slot-like perforations overlie identical slot-like perforations in adjacent facing support plates thereby forming continuous columns into which flowable sealing material is injected.

6. A separating device as defined by claim 5 wherein said facing adjacent support plates are inseparably connected by the solidified sealing material in said hollow space.

7. A separating device as defined by claim 6 wherein the sealing material comprises a thermally and chronologically age-hardenable plastic material.

* * * * *